United States Patent [19]
Riley

[11] Patent Number: 5,681,539
[45] Date of Patent: Oct. 28, 1997

[54] SURGICAL INSTRUMENT RETENTION BRACKET

[75] Inventor: Edward D. Riley, Falmouth, Me.

[73] Assignee: Riley Medical, Inc., Auburn, Me.

[21] Appl. No.: 653,991

[22] Filed: May 28, 1996

Related U.S. Application Data

[63] Continuation of Ser. No. 414,354, Mar. 31, 1995, abandoned, which is a continuation-in-part of Ser. No. 212,950, Mar. 15, 1994, Pat. No. 5,424,048.

[51] Int. Cl.$^6$ .................... A61L 2/26; B65D 85/20
[52] U.S. Cl. .................... 422/300; 422/297; 206/370; 206/443; 211/69
[58] Field of Search .................. 206/370, 438, 206/443; 422/297, 300; 211/69, 70.6, 70.7; 24/530, 545, 570

[56] References Cited

U.S. PATENT DOCUMENTS

| | | | |
|---|---|---|---|
| 337,888 | 3/1886 | Swan | 211/69 X |
| 635,284 | 10/1899 | Adair | 211/69 X |
| 4,135,868 | 1/1979 | Schainholz | 422/300 X |
| 4,317,416 | 3/1982 | Baum et al. | 248/223.1 |
| 4,573,569 | 3/1986 | Parker | 206/443 X |
| 4,643,303 | 2/1987 | Arp et al. | 422/300 X |
| 4,859,423 | 8/1989 | Perlman | 422/297 X |
| 5,433,930 | 7/1995 | Taschner | 206/370 X |
| 5,492,671 | 2/1996 | Krafft | 422/300 X |

*Primary Examiner*—Robert J. Warden
*Assistant Examiner*—E. Leigh Dawson
*Attorney, Agent, or Firm*—Cesari and McKenna, LLP

[57] ABSTRACT

A bracket for fixating medical instruments or other articles includes a base member with a plurality of spaced-apart fingers extending up from the base member. A recess is formed in a side wall of at least one finger, which recess faces the adjacent finger. Also, a sheath engages around each finger which sheath has a flexible, resilient side wall which overlies any recess in that finger and defines therewith a void. When an article is wedged into the space between the one and the adjacent finger, it will snap into a stable position opposite the void so that the article is resiliently engaged and fixated by the overlying sheath wall.

13 Claims, 2 Drawing Sheets

SURGICAL INSTRUMENT RETENTION BRACKET

RELATED APPLICATION

This application is a continuation of Ser. No. 08/414,354, filed Mar. 31, 1995, abandoned which is a continuation-in-part of Ser. No. 08/212,950, filed Mar. 15, 1994, now U.S. Pat. No. 5,424,048.

This invention relates to an instrument retention bracket. It relates especially to such a bracket capable of holding relatively heavy surgical instruments at fixed positions in a tray or other container.

BACKGROUND OF THE INVENTION

There does exit in the prior art various retaining means for fixing the positions of articles of one kind or another. These include hooks, pegs, clips, etc. The retention means with which we are primarily concerned here are of the clip type in that they resiliently engage the articles from opposite sides. Such retention means may be used in a wide variety of different applications. They are commonly used in the medical field to fix the positions of various articles while those articles are being transported and processed in one way or another. Accordingly, we will describe the invention in that context. It should be understood however, that the present invention has application in other fields besides the medical field.

Surgical instruments are often transported in trays. Prior to use, the instruments are placed in the tray and subjected to sterilization. In order to maintain a separation between the various instruments in the tray, they are supported or retained by brackets positioned in the tray. Following sterilization, the tray full of instruments may be transported to an operating room and placed close to the surgical team whose members may withdraw the instruments from the tray as needed for the particular surgical procedure being performed. Usually, the instruments are selectively arranged in the tray so that the instruments can be picked from the tray in the order that they are needed for the particular procedure. An example of such a tray is disclosed in the above U.S. Pat. No. 5,424,048 whose contents are hereby incorporated by reference herein.

As seen from the above application, the known retention means for fixating instruments in a tray include brackets comprising a relatively long blade of resilient material having a bottom flange which is releasably secured to the bottom wall of the tray at a selected location thereat. The bracket blades have slots or other openings which are adapted to receive surgical instruments so that the bracket resiliently grips the instruments. As shown there, a pair of such brackets can be spaced parallel in the tray so that they can engage and support the opposite ends of a set of different length instruments.

While such brackets are satisfactory for most applications, we have found that when relatively heavy instruments are supported in the tray by such brackets, if the tray is shaken or tilted, those instruments often become disengaged from their brackets and assume skewed positions in the tray so that they are difficult to remove without upsetting other instruments in the tray. In extreme cases, an instrument may even fall out of the tray and become contaminated. Since a tray may contain a complete set of instruments required for a particular surgical procedure, this may require that another full tray of sterilized instruments be made available to the surgical team.

It has been suggested that this problem be solved by making the instrument-retaining brackets of a stiffer material so that the instruments are gripped more firmly. However, that proposed solution makes it more difficult for the surgeon or nurse to quickly and easily remove the instruments from the tray when they are needed during an operation. Therefore, recourse to that solution may create a more serious problem.

Thus, there is thus a need, particularly in the medical field, for a bracket which can reliably fix the positions of medical instruments and other articles in a tray or to a surface, while permitting the quick release of those articles from the bracket.

SUMMARY OF THE INVENTION

Accordingly, the present invention aims to provide an improved bracket for releasably engaging a medical instrument or other article.

Another object of the invention is to provide a bracket of this type which can firmly retain a medical instrument or other article, yet permits the quick release of the instrument or article when necessary.

Another object of the invention is to provide such a bracket which is relatively easy and inexpensive to manufacture in quantity.

Still another object of the invention is to provide a bracket of this type which may be releasably mounted to a medical instrument tray or other support structure.

Other objects will, in part, be obvious and will, in part, appear hereinafter. The invention accordingly comprises the features of construction, combination of elements and arrangement of parts which will be exemplified in the following detailed description, and the scope of the invention will be indicated in the claims.

Briefly, my bracket includes a frame made of a relatively lightweight, rigid, material capable of withstanding sterilization temperatures. The frame includes a base strip which supports a linear array of upstanding fingers which are spaced apart along the strip. The spacing of the fingers is determined to a large extent by the size of the instruments or other articles which the bracket is intended to retain. Each bracket includes at least two fingers, the specific number of fingers being determined by the number of instruments or other articles that the bracket is intended to retain.

According to the invention, a side wall of a selected finger(s) is provided with one or more notches or recesses which face an adjacent finger which may or may not be notched. Also, snugly engaged on each finger of the bracket is a resilient cot or sheath having a side wall which normally bridges any notch or recess in the corresponding finger, thereby leaving a void in the bracket fingers at the location of each notch or recess, each such void constituting a seating site for an instrument. Alternatively, the sides of the sheaths may have portions or segments which are more compressible or softer than the remainders of the sheaths thereby forming the seating sites.

The bracket may simply rest on a support surface. More preferably, however, it should be releasably secured to that surface by suitable anchoring means at the underside of the base strip.

A single bracket may be used to retain relatively short instruments or other articles. The retention of longer instruments or articles may require that a pair of such brackets be spaced parallel to one another so that the brackets can releasably engage opposite ends of the longer instruments or articles, the bracket spacing being determined by the lengths of the instruments.

The bracket is used by wedging the instruments to be retained between adjacent fingers of the bracket. At the location of each seating site, a side of the resilient sheath is deformed thereby providing clearance for an instrument. Resultantly, the instrument "snaps" into a stable position between the adjacent fingers. If the seating site is a void which is closed so as to form an air pocket, that air is compressed so that it exerts an outward force on the sheath thereby helping to press the sheath wall into engagement with the instrument. This compressive engagement of the instrument by the finger sheaths securely retains the instruments in place between the bracket fingers, yet permits their ready removal in the event that becomes necessary or desirable.

The frame component of the bracket may be a simple molded plastic part that can be made in quantity at relatively low cost. The finger sheaths may also be molded of a suitable inexpensive resilient plastic material capable of withstanding sterilization temperatures. Therefore, the bracket as a whole is relatively economical to make and should find wide application particularly in the medical industry where the retention of instruments and other articles is of some importance.

BRIEF DESCRIPTION OF THE DRAWINGS

For a fuller understanding of the nature and objects of the invention, reference should be had to the following detailed description taken in connection with the accompanying drawings, in which.

DESCRIPTION OF THE PREFERRED EMBODIMENTS

Figure 1:
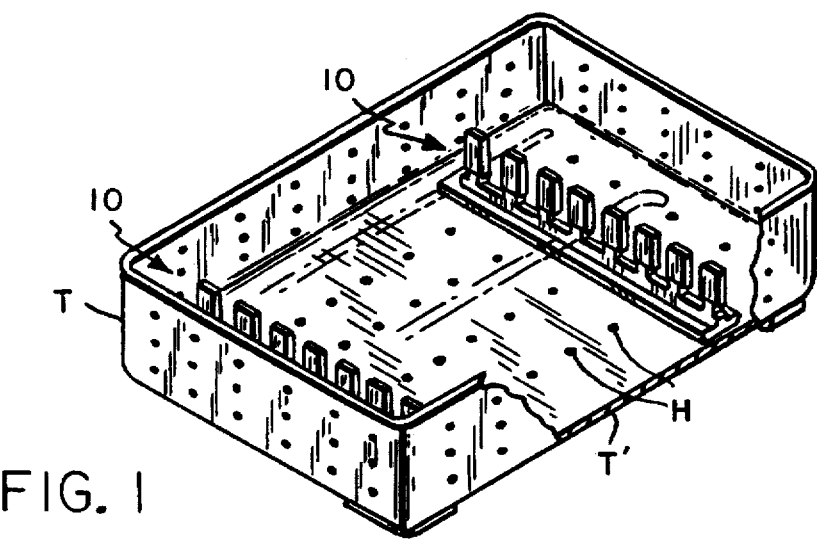
FIG. 1 is a perspective view with parts broken away of a tray containing surgical instruments fixated by brackets made in accordance with this invention.

Refer to FIG. 1 of the drawings which illustrates a generally rectangular medical tray T having a bottom wall T' containing an array of small through-holes H. Positioned in tray T is a pair of brackets shown generally at 10 which are releasably anchored to bottom wall T' by anchoring means to be described later. The brackets 10 are spaced parallel to one another in the tray and are arranged to firmly fixate certain instruments I in the tray even if the tray is tilted or turned upside down, yet to readily release the instruments I when they are needed by a surgeon or other person.

Figure 2:
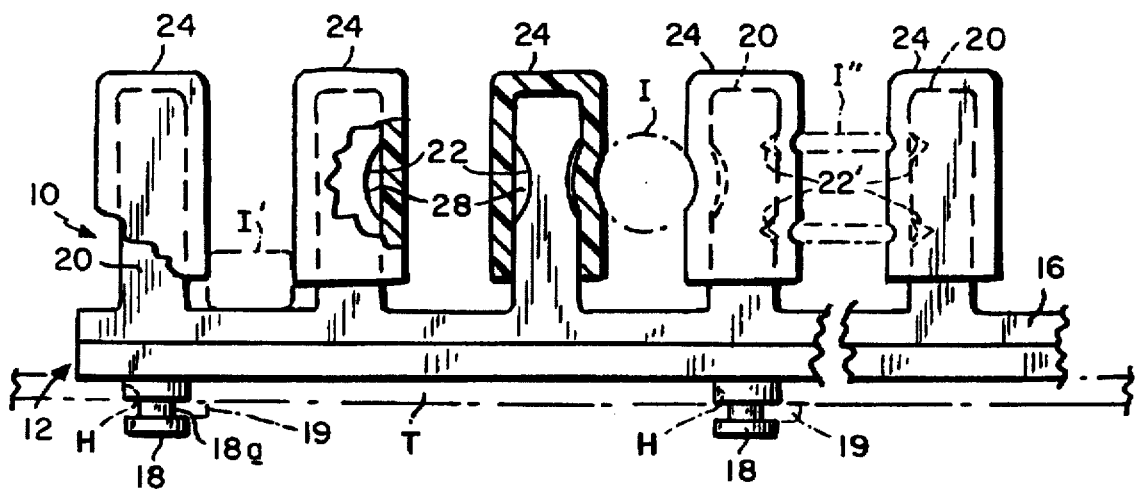
FIG. 2 is a side elevational view with parts broken away on a larger scale showing a bracket in greater detail.
Figure 3:
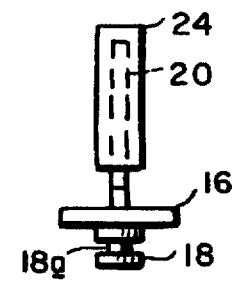
FIG. 3 is an end view of the FIG. 2 bracket.
Figure 4:
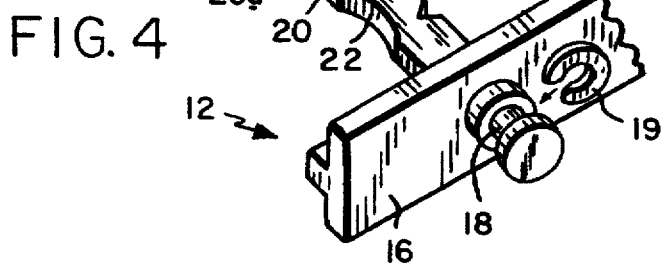
FIG. 4 is a fragmentary exploded perspective view on a still larger scale showing the components of my bracket in still greater detail.

Referring now to FIGS. 2 to 4, each bracket 10 comprises a frame shown generally at 12 which may be of a suitable, rigid metal or plastic material. Preferably the frame is of polyetherimide or polyphenylsulfone so that it is able to withstand sterilization temperatures and can be made in quantity relatively inexpensively using conventional molding processes. Frame 12 comprises a generally rectangular base strip 16 which can be of any desired length. Spaced along the underside of strip 16 at the centerline thereof is a linear array of small diameter cylindrical posts 18 having reduced diameter necks 18a. These posts are dimensioned and disposed along strip 16 so that they can be received in the holes H in the tray T depicted in FIG. 1. Frame 12 may be releasably anchored to the tray bottom wall T' by engaging conventional C-clips 19 around the post necks 18a that project below the tray wall T' as shown in FIG. 2.

Projecting up from base strip 16 preferably opposite selected posts 18 is a linear array of upstanding fingers 20. The illustrated fingers 20 are shaped like tabs or paddles; however, other shapes, e.g., cylindrical are possible. Typically, the fingers are about 1.5 in. high and 0.5 in. wide. While the illustrated fingers 20 are shown as being equally spaced apart along the base strip 16, the adjacent fingers 20 may have different spacings so that the bracket 10 can retain different sized instruments or other articles. The numbers of fingers 20 projecting up from base strip 16 depends upon the length of the base strip and the sizes of the instruments to be retained by the bracket. In any event, each bracket 10 includes at least a pair of upstanding fingers 20.

As best seen in FIG. 4, the side edges 20a, i.e., the edges facing adjacent fingers, are slightly undercut or tapered so that the finger is the general shape of a trapezoid. Also, a notch or recess 22 may be formed in the side wall(s) 20a in one or more of the fingers 20 so that the notch faces the adjacent finger. These notches or recesses may have various shapes. The notches 22 are arcuate; however, they could just as well be wedge-shaped as shown at 22' in FIGS. 2 and 4.

Still referring to FIGS. 2 to 4, bracket 10 also includes a set of resilient sheaths 24 which snugly engage around the fingers 20 of bracket 10 and have relatively thick walls, e.g., ⅛ in. The illustrated sheaths 24 are formed as cots in that they have top walls. However, they could just as well be sleeves which tightly encircle the fingers. The illustrated sheaths 24 are generally rectangular to conform to the shape of the flat fingers 20. Obviously, if the fingers were cylindrical, the sheaths would be also. The sheaths 24 are preferably molded of a suitable, flexible, resilient material, such as silicone, which is able to withstand sterilization temperatures.

The sheaths 24 have central openings 26 which are shaped and dimensioned so that the sheaths fit snugly on the fingers 20 with a slight amount of stretch of the sheath walls. As noted above, the illustrated fingers 20 have tapered side walls so that the sheaths can contract slightly at the narrower roots of the fingers. Consequently, the sheaths tend to remain on the fingers unless they are forcibly removed.

As best seen in FIG. 2, when the sheaths 24 are properly placed on the fingers 20, a void 28 may exists under the sheath at the location of each finger notch or recess 22, 22'. Each void 28 provides a stable seating site for an instrument I.

After the bracket 10 has been anchored to a supporting surface such as the bottom wall T' of tray T depicted in FIG. 1, instruments I may be wedged between the adjacent fingers of the bracket frame. Obviously, if the bracket is to be effective, the width of a particular instrument I should be slightly wider than the space between the particular finger pair in question. As the instrument I is wedged into place between the fingers, the opposing walls of the sheaths 24 may be compressed to some extent to allow passage of the instrument into the space between the fingers.

As the instrument is pressed down toward base strip 16, when the instrument moves opposite the void 28, the instrument collapses the sheath walls into the associated finger notches or recesses 22 so that the instrument snaps into place between the fingers. The sheath walls tend to resume their undistorted shapes. Also, the collapsing of the sheath walls compresses any trapped air in the voids 28 so that the air exerts an outward force on the sheath wall. Resultantly, the sheath resiliently engages around the instrument and firmly grips the instrument between the operative pair of fingers. Yet, the finger sheath will readily release the instrument in response to an upward pulling force by a surgeon or other person.

The bracket 10 illustrated in FIG. 2 is designed to retain a single instrument between the fingers 20 having the opposed crescent-shape cutouts 22 as shown in phantom at I in that figure.

In some cases, the finger undercut or taper itself may constitute the recess in that finger. For example, the pair of fingers at the left hand end of bracket 10 in FIG. 2 are able to retain a generally rectangular instrument shown in phantom at I' because the wedging of the instrument between the two fingers collapses the sheath walls against the undercut sidewalls 20a of the fingers so that the instrument I' is resiliently engaged or gripped by the sheaths 24 which tend to assume their normal undistorted rectilinear shapes.

The two fingers at the right hand end of bracket 10 in FIG. 2 have pairs of generally wedge shaped notches 22' enabling those fingers to releasably retain a pair of blade-like instruments I" arranged one on top of the other.

Preferably, the sheaths 24 are removable from their respective fingers 20 so that sheaths having different wall thickness can be positioned on frame 12. This effectively changes the width of the space between the fingers thereby enabling the same frame to be used to retain or fixate instruments having different widths.

Figure 5:
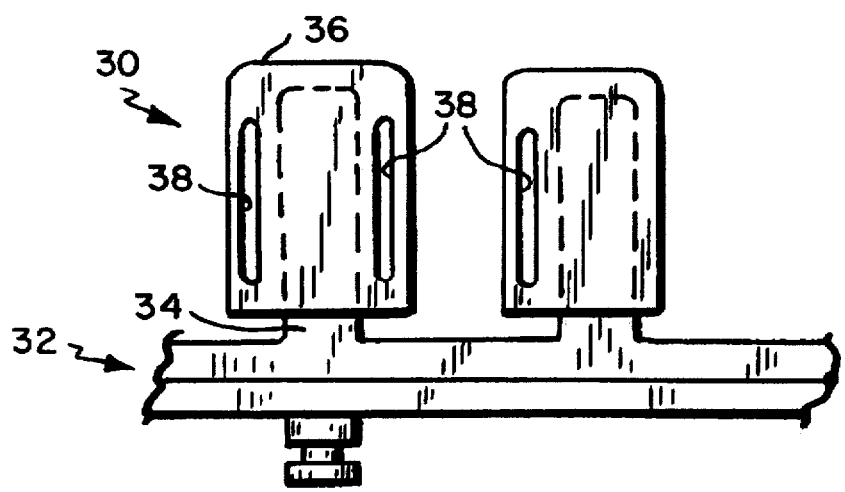
FIG. 5 is a view similar to FIG. 2 of another bracket embodiment.

Refer now to FIG. 5, which shows a bracket 30 whose frame 32 has fingers 34 with no notches 22. Rather, the fingers are encircled by resilient sheaths 36 having vertically oriented-lateral through-slits 38 adjacent to one or both of the sheath side edges.

When an instrument is wedged between the adjacent fingers 34, the side walls of one or both sheaths will collapse into the slit 38 which functions like the void 28 described above in connection with bracket 10.

Figure 6:
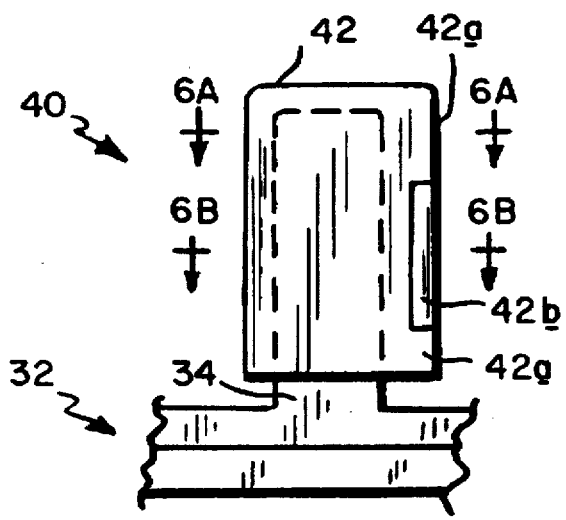
FIG. 6 is a view similar to FIG. 2 of still another bracket embodiment.
Figure 6A:
FIGS. 6A and 6B are sectional views taken along lines 6A—6A and 6B—6B, of FIG. 6.
Figure 6B:
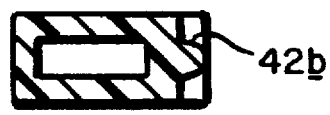

FIGS. 6, 6A and 6B illustrate still another bracket 40 which also includes a frame 32. However, it has a sheath 42 on each frame finger 34 that has a varying thickness sidewall (s). Near the top and bottom of the sheath the sidewall is relatively thick as shown at 42a. However, in the middle segment of the finger, the sidewall is thin and narrow as shown at 42b. Therefore, that segment 42b is more compressive and tends to collapse when an instrument is wedged into the space adjacent to that sidewall so that the sheath resiliently engages the instrument. Thus, that segment 42b functions as a seating site just as described above for brackets 10 and 30.

To use the brackets 10, 30 and 40 singly or in multiples, the bracket(s) is positioned on its supporting surface as depicted in FIG. 1 so that the bracket fingers are aligned. Then, the instruments or other articles are pressed down into the spaces between the bracket fingers until they snap into place opposite the voids 28 or other seating sites at the sides of the fingers. When seated thusly, the instruments will remain in position even though the support surface is moved about, tilted or even inverted. Thus, the instruments will always be in the correct position when presented to a surgeon or nurse. Yet, the instruments can be removed easily from the brackets by a gentle upward pulling force which suffices to compress the sheath 24 walls near the upper ends of the fingers sufficiently to enable the instruments to be withdrawn from the bracket.

As described above, the bracket may be made quite easily using conventional molding materials and techniques. Therefore, it should find wide application, particularly in the medical field.

It will thus be seen that the objects set forth above, among those made apparent from the preceding description, are efficiently attained and, since certain changes may be made in the above constructions without departing from the scope of the invention, it is intended that all matter contained in the above description of shown in the accompanying drawings shall be interpreted as illustrative and not in a limiting sense.

It is also to be understood that the following claims are intended to cover all of the generic and specific features of the invention described herein.

What is claimed is:

1. A bracket for fixating medical instruments or other articles, said bracket comprising
   a rigid frame, said frame including
      a base member,
      a plurality of spaced-apart adjacent upstanding fingers integral to the base member, each finger having opposite sides and
      means defining a recess in the side of at least one finger, said recess facing the adjacent finger, and
   a resilient sheath tightly engaged around said at least one finger, said sheath having a flexible, resilient sidewall which overlies any recess in that finger and defines therewith a void which is bridged by a portion of said sidewall so that when an article is forced into the space between said one and said adjacent finger, the article will snap into a stable position opposite the void and be resiliently engaged and fixated by said overlying sidewall.

2. The bracket defined in claim 1 wherein each sheath comprises a cot of flexible, resilient plastic material.

3. The bracket defined in claim 2 wherein said fingers and said cots are substantially rectangular in shape.

4. The bracket defined in claim 3 wherein said finger sidewalls are tapered.

5. The bracket defined in claim 1 wherein said base member is of a rigid molded plastic material.

6. The bracket defined in claim 5 wherein said base member is of polyetherimide or polyphenylsulfane and said cots are of silicone.

7. The bracket defined in claim 1 and further including means on said base member for releasably anchoring said bracket to a support surface.

8. The bracket defined in claim 7 wherein said anchoring means comprise
   a series of posts spaced along said base on the opposite side thereof from said fingers, each of said posts having a constriction along its length, and
   a clip for resiliently engaging around each constriction.

9. The bracket defined in claim 1 wherein said void is closed and forms an air pocket.

10. A bracket for retaining medical instruments or other articles, said bracket comprising
    a rigid frame, said frame including
       a base member and
       a plurality of spaced-apart adjacent upstanding fingers integral to the base member;
    a sheath tightly surrounding each finger, each sheath having opposite side walls, and means defining a compressive instrument seating site along a selected sidewall of at least one sheath so that when an instrument is forced into the space between the selected sidewall of said at least one sheath and the adjacent sheath, the instrument will snap into a stable position at the seating site and be resiliently engaged and fixated by said selected sidewall.

11. A bracket for retaining medical instruments or other articles, said bracket comprising a plurality of adjacent rigid finger members;

means for rigidly mounting said finger members to a support so that adjacent finger members are spaced apart a selected distance and are substantially parallel to one another;

a resilient sheath tightly surrounding each finger member, each sheath having opposite side walls, and means defining a compressive instrument seating site along a selected sidewall of at least one sheath said seating site being defined by a recess in the finger member underlying the selected sidewall and a portion of the sidewall that bridges said recess so that when an instrument is forced into the space between the selected sidewall of said at least one sheath and the adjacent sheath, the instrument will snap into a stable position at the seating site and be resiliently engaged and fixated by said selected side wall.

12. A bracket for retaining medical instruments or other articles, said bracket comprising a rigid frame, said frame including
a base member and
a plurality of spaced-apart adjacent upstanding fingers integral to the base member;

a resilient sheath tightly surrounding each finger, each sheath having opposite sidewalls, and means defining a compressive instrument seating site along a selected sidewall of at least one sheath said seating site being defined by a void in or under said selected sidewall and a sidewall portion that bridges said void so that when an instrument is forced into the space between the selected sidewall of said at least one sheath and the adjacent sheath, the instrument will snap into a stable position at the seating site and be resiliently engaged and fixated by said selected sidewall.

13. A bracket for retaining medical instruments or other articles, said bracket comprising a base member;

a plurality of spaced-apart, adjacent, substantially straight fingers extending up from the base member;

a resilient sheath tightly surrounding each finger, each sheath having opposite sidewalls, and means defining a compressive instrument seating site along a selected sidewall of at least one sheath, said seating site being defined by a reduced width segment of said selected sidewall, so that when an instrument is forced into the space between the selected sidewall of said at least one sheath and the adjacent sheath, the instrument will snap into a stable position at the seating site and be resiliently engaged and fixated by said selected sidewall.

* * * * *